United States Patent [19]

Holland et al.

[11] Patent Number: 4,902,694

[45] Date of Patent: Feb. 20, 1990

[54] DIHYDROPYRIDINE CALCIUM CHANNEL MODULATORS

[75] Inventors: Donald R. Holland, Indianapolis; James H. Wikel, Greenwood, both of Ind.

[73] Assignee: Eli Lilly and Company, Indianapolis, Ind.

[21] Appl. No.: 231,310

[22] Filed: Aug. 11, 1988

[51] Int. Cl.$^4$ ............... A61K 31/44; C07D 495/04
[52] U.S. Cl. ............................. 514/301; 546/114
[58] Field of Search ....................... 546/114; 514/301

[56] References Cited

U.S. PATENT DOCUMENTS 4,659,717  4/1987  Wikel .................................. 546/114

OTHER PUBLICATIONS

Manuscript entitled *LY249933: A Cardioselective 1,4-Dihydropyridine with Positive Inotropic Activity*, (1988).

*Primary Examiner*—Mary C. Lee
*Assistant Examiner*—Bernard I. Dentz
*Attorney, Agent, or Firm*—Joseph A. Jones; Leroy Whitaker; Edward P. Gray

[57] ABSTRACT

4-[Thieno[3,2-c]pyridinyl]-pyridinecarboxylic acid esters as calcium channel modulators, methods of use and pharmaceutical compositions therefor.

12 Claims, No Drawings

DIHYDROPYRIDINE CALCIUM CHANNEL MODULATORS

BACKGROUND OF THE INVENTION

Over the past two decades, a number of calcium channel antagonists of the 1,4-dihydropyridine class have been identified that bind to calcium channels and inhibit calcium flux. Another group of compounds, the more recently identified calcium agonists are also 1,4-dihydropyridines that bind to the calcium channel but increase calcium flux. The expression of agonist or antagonist activities of the dihydropyridines appears to be dependent both on transmembrane potential of the target cell and drug concentration.

The compounds of the present invention are 1,4-dihydropyridines which exhibit the ability to modulate calcium flux across calcium channels. These compounds exhibit beneficial cardiovascular activities such as increasing cardiac contractibility, decreasing heart rate, decreasing vascular resistance, decreasing rate pressure product (as an index of oxygen consumption) or producing class III antiarrhythmic activity. This pharmacological profile makes these compounds useful in cardiovascular diseases such as congestive heart failure.

SUMMARY OF THE INVENTION

The present invention is directed to a compound of the formula I

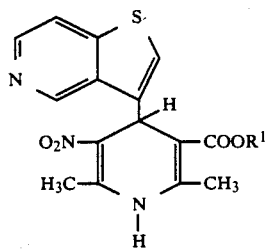

and pharmaceutically acceptable salts thereof wherein $R^1$ is $C_1$-$C_6$ alkyl optionally substituted with one or more groups selected from phenyl, methoxy-substituted phenyl, phenoxy, methoxy or cyclopropyl; or $R^1$ is cyanoethyl.

Also disclosed and claimed is a method of treating congestive heart failure in a mammal in need thereof by administering to said mammal an effective amount of a compound of formula I. Further, pharmaceutical formulations for use in treating congestive heart failure are provided comprising an effective amount of a compound of formula I, or a pharmaceutically acceptable salt thereof in admixture with one or more pharmaceutically acceptable carriers, diluents or excipients therefor.

As used herein, the term "$C_1$-$C_6$ alkyl" refers to straight or branched chain aliphatic radicals (saturated or unsaturated) containing from one to six carbon atoms, both inclusive. Thus, "$C_1$-$C_6$ alkyl" includes radicals such as methyl, ethyl, propyl, isopropyl, butyl, sec-butyl, propynyl, butynyl, 1-methyl-2-butynyl, 1,2,2-trimethylpropyl, pentyl, neopentyl, hexyl and the like. Thus, $C_1$-$C_6$ alkyl optionally substituted as provided for above includes radicals such as 2-methyl-1-phenylpropyl, 4-methoxyphenylmethyl, 3-phenyl-2-propynyl, cyclopropylmethyl and the like.

Preferred compounds of the present invention are 1,4-dihydro-2,6-dimethyl-5-nitro-4-[thieno[3,2-c]-pyridin-3-yl]-3-pyridinecarboxylic acid, 1-phenylethyl ester; 1,4-dihydro-2,6-dimethyl-5-nitro-4-[thieno[3,2-c]-pyridin-3-yl]-3-pyridinecarboxylic acid, 1-methyl-2-propynyl ester; and 1,4-dihydro-2,6-dimethyl-5-nitro-4-[3,2-c]pyridin-3-yl]-3-pyridinecarboxylic acid, cyclopropylmethyl ester.

As will be recognized by those skilled in the art, the compounds of formula I may contain one or more asymmetric carbon atoms. The present invention is not limited to any particular isomer but includes all individual isomers as well as all isomeric mixtures and racemates.

The pharmaceutically acceptable salts of the compounds of formula I can be prepared employing those acids of sufficient acidity to form acid addition salts. These acids include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

DETAILED DESCRIPTION OF THE INVENTION

The compounds of the present invention may be prepared by any of a number of methods known in the art. For example, compounds of formula I may be prepared by the reaction of approximately equimolar amounts of intermediate II:

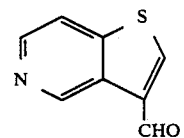

with intermediate III:

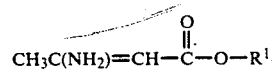

with nitroacetone. The reaction is generally carried out in a non-reactive solvent such as an alcohol or preferably, an aprotic solvent such as tetrahydrofuran (THF) or dimethylformamide (DMF). The reaction is typically carried out at a temperature from about 20° C. up to the reflux temperature of the reaction mixture for a time sufficient to complete the reaction, typically from about 2 to about 6 hours.

Intermediates II and III are either commercially available, are known in the literature or are prepared by methods taught in the literature. For example, the aldehyde intermediate II may be conveniently prepared according to the following reaction scheme:

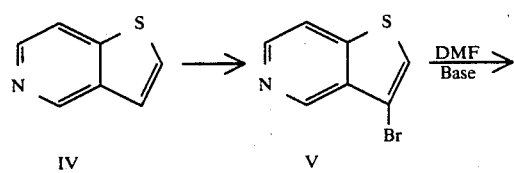

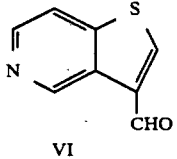

VI

The bromo intermediate V is prepared from the unsubstituted intermediate IV by reaction with bromine and hydrobromic acid at a temperature of about 100° C. for a time sufficient to effect bromination, typically from about 6 to about 10 hours. This bromo intermediate is then transformed into aldehyde VI by treatment with dimethylformamide and a strong base such as n-butyl lithium and a non-reactive solvent such as diethyl ether or THF at temperatures from about −40° to about 0° C. Similarly, the 3-aminocrotonate ester intermediates (III) are readily prepared from diketene (i.e., acetyl ketene) or Meldrum's Acid (i.e., isopropylidene malonate) and the appropriate $R^1$-containing alcohol by well-known methodologies. See, for example, Oikawa et al., *J. Org. Chem.* 43, 10, 2087–2088 (1978) which is incorporated herein by reference.

The following examples are provided as a means of illustrating the present invention and are not to be construed as a limitation thereon.

EXAMPLE 1

1,4-Dihydro-2,6-dimethyl-5-nitro-4-[thieno-[3,2-c]pyridin-3-yl]-3-pyridinecarboxylic acid, butyl ester

A. Preparation of 3-bromothieno[3,2-c]pyridine

To a solution of 5.4 g of thieno[3,2-c]pyridine and 120 ml of 48% (w/w) hydrobromic acid was added a solution of 4.4 ml of bromine in 60 ml of 48% (w/w) hydrobromic acid. A solid precipitated out of solution and the resultant mixture was maintained at 105° C. for 6 hours in a sealed vessel after which it was allowed to cool to room temperature overnight. The mixture was then poured over ice layered with methylene chloride and the mixture was made basic (pH9) with ammonium hydroxide. The layers were separated and the aqueous layer was extracted two times with methylene chloride. The combined extracts were refrigerated overnight and then dried over magnesium sulfate to render a tan solid, a portion of which was taken up in 300 ml of diethyl ether. An insoluble material formed and was removed by filtration. The diethyl ether was concentrated to about 50 ml from which crystals of the desired subtitle intermediate formed and were collected.

Analysis for $C_7H_4NBrS$: Calculated: C, 39.27; H, 1.88; N, 6.54; Found: C, 39.32; H, 1.83; N, 6.38.

B. Preparation of thieno[3,2-c]pyridine-3-carboxaldehyde

To 2.14 g of 3-bromothieno[3,2-c]pyridine prepared as described above was added 150 ml of dry diethyl ether. The solution was stirred at room temperature for 15 minutes after which the temperature was gradually reduced to −70° C. and 6.5 ml of n-butyl lithium (1.6 molar) was added. The mixture was stirred for 30 minutes at −70° C. at which time a solution of 0.8 ml DMF in 20 ml of diethyl ether was added. This mixture was then stirred for an additional 1 hour and then allowed to warm to 0° C. at which time 3 ml of glacial acetic acid was added. The ether was removed via vacuum resulting in an oil which was taken up in approximately 400 ml of a mixture of 1N hydrochloric acid and water (pH adjusted to 1.5). This mixture was extracted with methylene chloride and the extract discarded. The pH of the mixture was adjusted to pH 11 and extracted a second time with methylene chloride. The extract was dried over magnesium sulfate and reduced to an oil via vacuum. The oil was taken up in hexane resulting in the formation of crystals of the desired subtitle intermediate which were collected and used as described below.

Analysis for $C_8H_5NOS$: Calculated: C, 58.88; H, 3.09; N, 8.58; Found: C, 58.94; H, 3.02; N, 8.41.

C. Preparation of 1,4-dihydro-2,6-dimethyl-5-nitro-4-[thieno(3,2-c)pyridin-3-yl]-3-pyridinecarboxylic acid, butyl ester A mixture of 2 g thieno[3,2-c]-3-carboxaldehyde, 2 g of n-butyl-aminocrotonate and 2 g of nitroacetone in 50 ml of THF was heated to a gentle reflux overnight. The mixture was allowed to cool to room temperature and the solvent was then removed by vacuum to render an oil which was dissolved in 75 ml of methylene chloride and chromatographed on a Waters Associates Prep 500 using 50% methylene chloride/ethyl acetate as an eluant. The solvent was removed to give a foam which was taken up in diethyl ether and triturated to yield a solid which was collected by filtration providing 1.3 g (27% yield) of the desired title product, melting point (m.p.) 213°–214° C.

Analysis for $C_{29}H_{21}N_3O_4S$: Calculated: C, 58.90; H, 5.46, N, 10.85; Found: C, 59.11; H, 5.22, N, 11.10.

EXAMPLES 2–12

Following the procedures of Example 1, the following compounds were prepared from thieno[3,2-c]-pyridine-3-carboxaldehyde, nitroacetone and the appropriate $R^1$-3-aminocrotonate ester.

2. (S)-1,4-Dihydro-2,6-dimethyl-5-nitro-4-[thieno[3,2-c]pyridin-3-yl]-3-pyridinecarboxylic acid, 1-methylpropyl ester, 25% yield, m.p. 218°–219° C.

Analysis for $C_{19}H_{21}N_3O_4S$: Calculated: C, 58.90; H, 5.46; N, 10.85; Found: C, 59.00; H, 5.68; N, 10.89.

3. 1,4-Dihydro-2,6-dimethyl-5-nitro-4-thieno[3,2-c]-pyridin-3-yl]-3-pyridinecarboxylic acid, methyl ester, 19% yield, m.p. 238–239.

Analysis for $C_{16}H_{15}N_3O_4S$: Calculated: C, 55.65; H, 4.35; N, 12.17; Found: C, 56.05; h, 4.47; N, 12.14.

4. 1,4-Dihydro-2,6-dimethyl-5-nitro-4-[thieno[3,2-c]-pyridin-3-yl]-3-pyridinecarboxylic acid, 1-methylethyl ester, 25% yield, m.p. 233°–235° C.

Analysis for $C_{18}H_{19}N_3O_4S$: Calculated: C, 57.90; H, 5 13; N, 11.25 Found: C, 57.67; H, 4.85; N, 11.29

5. 1,4-Dihydro-2,6-dimethyl-5-nitro-4-thieno[3,2-c]-pyridin-3-yl]-3-pyridinecarboxylic acid, 2-propynyl ester, 6.6% yield, m.p. 188°–191° C.

Analysis for $C_{18}H_{15}N_3O_4S$: Calculated: C, 58.53; H, 4.09; N, 11.38 Found: C, 58.71; H, 4.19; N, 11.12

6. 1,4-Dihydro-2,6-dimethyl-5-nitro-4-[thieno[3,2-c]-pyridin-3-yl]-3-pyridinecarboxylic acid, 1-methyl-2-propynyl ester, 21% yield, m.p. 217°–219° C.

Analysis for $C_{19}H_{17}N_3O_4S$: Calculated: C, 59.53; H, 4.43; N, 10.96; Found: C, 60.60; H, 4.46; N, 11.06.

7. 1,4-Dihydro-2,6-dimethyl-5-nitro-4-[thieno[3,2-c]-pyridin-3-yl]-3-pyridinecarboxylic acid, 2-butynyl ester, 23% yield, m.p. 218°–219° C.

Analysis for $C_{19}H_{17}N_3O_4S$: Calculated: C, 59.52; H, 4.47; N, 10.96; Found: C, 59.71; H, 4.57; N, 11.23.

8. 1,4-Dihydro-2,6-dimethyl-5-nitro-4-[thieno[3,2-c]-pyridin-3-yl]-3-pyridinecarboxylic acid, 1-methyl-2-butynyl ester, 31% yield, m.p. 204°-205° C.

Analysis for $C_{20}H_{19}N_3O_4S$: Calculated: C, 60.44; H, 4.82; „ 10.57; Found: C, 60.40; H, 4.72; N, 10.43.

9. 1,4-Dihydro-2,6-dimethyl-5-nitro-4-[thieno[3,2-c]-pyridin-3-yl]-3-pyridinecarboxylic acid, 2,2-dimethylpropyl ester, 25% yield, m.p. 213°-215° C.

Analysis for $C_{20}H_{23}N_3O_4S$: Calculated: C, 59.83; H, 5.77; N, 10.47; Found: C, 59.62; H, 5.74; N, 10.21.

10. 1,4-Dihydro-2,6-dimethyl-5-nitro-4-thieno[3,2-c]-pyridin-3-yl]-3-pyridinecarboxylic acid, 3-butynyl ester, 26% yield, m.p. 216°-219° C.

Analysis for $C_{19}H_{17}N_3O_4S$: Calculated: C, 59.52; H, 4.47; N, 10.96; Found: C, 59.23; H, 4.72; N, 11.05.

11. 1,4-Dihydro-2,6-dimethyl-5-nitro-4-[thieno3,2-c]-pyridin-3-yl]-3-pyridinecarboxylic acid, 1,1-dimethyl-2-propynyl ester, 25% yield, m.p. 229°-230° C.

Analysis for $C_{20}H_{19}N_3O_4S$: Calculated: C, 61.30; H, 5.14; N, 10.21; Found: C, 61.02; H, 4.90; N, 10.17.

12. 1,4-Dihydro-2,6-dimethyl-5-nitro-4-[thieno3,2-c]-pyridin-3-yl-3-pyridinecarboxylic acid, 1,2,2-trimethylpropyl ester, 28% yield, m.p. 213°-215° C.

Analysis for $C_{21}H_{25}N_3O_4S$: Calculated: C, 60.70; H, 6.06; N, 10.11; Found: C, 60.97; H, 6.26; N, 10.23.

EXAMPLE 13

R(+)-1,4-Dihydro-2,6-dimethyl-5-nitro-4-[thieno[3,2-c]pyridin-3-yl]-3-pyridinecarboxylic acid, (2Amethyl-1-phenylpropyl) ester.

Thieno[3,2-c]pyridine-3-carboxaldehyde (2 g), nitroacetone (2 g) and 2 g of R(+)-2-methyl-1-phenylpropylaminocrotonate in 50 ml of THF were heated to a gentle reflux overnight. The mixture was allowed to cool to room temperature to render an oil which was subsequently worked up as described in Example 1C to yield the desired title compound (35% yield), m.p. 232°-234° C.

Analysis for $C_{25}H_{25}N_3O_4S$: Calculated: C, 64,78; H, 5.44; N, 9.06; Found: C, 64.77; H, 5.51; N, 8.83.

Utilizing the procedures set forth herein, the following additional compounds were prepared.

14. S-(-)-1,4-Dihydro-2,6-dimethyl-5-nitro-4-[thieno[3,2-c]pyridin-3-yl]-3-pyridinecarboxylic acid, 2-methyl-1-phenylpropyl ester, 29% yield, m.p. 224-227.

Analysis for $C_{25}H_{25}N_3O_4S$: Calculated: C, 64.78; H, 5.44; N, 9.06; Found: C, 64.53; H, 5.56; N, 8.87.

15. 1,4-Dihydro-2,6-dimethyl-5-nitro-4-[thieno[3,2-c]-pyridin-3-yl]-3-pyridinecarboxylic acid, 1-methyl-1phenylethyl ester, 35% yield, m.p. 185°-186° C.

Analysis for $C_{24}H_{23}N_3O_4S$: Calculated: C, 64.13; H, 5.16; N, 9.35; Found: C, 64.23; H, 5.31; N, 9.17.

16. (R,d)-1,4-Dihydro-2,6-dimethyl-5-nitro-4-[thieno-[3,2-c]pyridin-3-yl]-3-pyridinecarboxylic acid, 1-phenylethyl ester, m.p. 226-228

Analysis for $C_{24}H_{23}N_3O_4S$: Calculated: C, 63.43: H, 4.86; N. 9.65; Found: C, 63.41; H, 5.01; N, 9.36.

17. (R,l)-1,4-Dihydro-2,6-dimethyl-5-nitro-4-[thieno-[3,2-c]pyridin-3-yl]-3-pyridinecarboxylic acid, 1-phenylethyl ester, m.p. 205-207.

Analysis for $C_{24}H_{23}N_3O_4S$: Calculated: C, 63.43; H, 4.86; N, 9.65; Found: C, 63.43; H, 4.73; N, 9.68.

18. 1,4-Dihydro-2,6-dimethyl-5-nitro-4-[thieno[3,2-c]-pyridin-3-yl]-3-pyridinecarboxylic acid, (1-phenylpropyl)ester, 22% yield, m.p. 221°-223° C.

Analysis for $C_{24}H_{23}N_3O_4S$: Calculated: C, 64.13; H, 5.16; N, 9.35; Found: C, 64.27; H, 5.32; N, 9.26.

19. 1,4-Dihydro-2,6-dimethyl-5-nitro-4-[thieno[3,2-c]-pyridin-3-yl]-3-pyridinecarboxylic acid, (4-methoxyphenyl)methyl ester, 18% yield, m.p. 222-223.

Analysis for $C_{23}H_{21}N_3O_5S$: Calculated: C, 61.19; H, 4.69: N. 9.31: Found: C, 60.96; H, 4.90; N, 9.13.

20. 1,4-Dihydro-2,6-dimethyl-5-nitro-4-[thieno[3,2-c]-pyridin-3-yl]-3-pyridinecarboxylic acid, 1-methyl-2-phenylethyl ester, 22% yield, m.p. 208°-210° C.

Analysis for $C_{24}H_{23}N_3O_4S$: Calculated: C, 64.12; H, 5.16; N, 9.35; Found: C, 63.88; H, 5.29; N, 9.08.

21. 1,4-Dihydro-2,6-dimethyl-5-nitro-4-[thieno[3,2-c]-pyridin-3-yl]-3-pyridinecarboxylic acid, 2-phenylpropyl ester, 27% yield, m.p. 198°-199° C.

Analysis for $C_{24}H_{23}N_3O_4S$: Calculated: C, 64.13; H, 5.16; N, 9.35; Found: C, 64.37; H, 5.20; N, 9.34.

22. 1,4-Dihydro-2,6-dimethyl-5-nitro-4-[thieno[3,2-c]-pyridin-3-yl]-3-pyridinecarboxylic acid, phenylmethyl ester, 25% yield, m.p. 211-214.

Analysis for $C_{22}H_{19}N_3O_4S$: Calculated: C, 62.70: H, 4.54: N, 9.97; Found: C, 62.70: H, 4.71; N, 9.76.

23. 1,4-Dihydro-2,6-dimethyl-5-nitro-4-[thieno[3,2-c]-pyridin-3-yl]-3-pyridinecarboxylic acid, 2-phenoxyethyl ester, 8% yield, m.p. 206°-208° C.

Analysis for $C_{23}H_{21}N_3O_5S$: Calculated: C, 61.lg H, 4.69: N, g 31: Found: C, 61.16 H, 4.55: N, 9.02.

24. 1,4-Dihydro-2,6-dimethyl-5-nitro-4-thieno3,2-c]-pyridin-3-yl]-3-pyridinecarboxylic acid, 3-phenyl-2-propynyl ester, 27% yield, m.p. 215°-216° C.

Analysis for $C_{24}H_{19}N_3O_4S$: Calculated: C, 64.71; H, 4.30; N, 9.43; Found: C, 64.96; H, 4.32; N, 9.51.

25. 1,4-Dihydro-2,6-dimethyl-5-nitro-4-[thieno[3,2-c]-pyridin-3-yl]-3-pyridinecarboxylic acid, 2-methoxy-2-phenylethyl ester, 25% yield, m.p. 208-211.

Analysis for $C_{24}H_{23}N_3O_5S$: Calculated: C, 61.92; H, 4.98; N, 9.03; Found: C, 62.07; H, 5.09; N, 9.95.

26. (S)-1,4-Dihydro-2,6-dimethyl-5-nitro-4-[thieno-[3,2-c]pyridin-3-yl]-3-pyridinecarboxylic acid, 1-phenylethyl ester, 28% yield, m.p. 219-221.

Analysis for $C_{23}H_{21}N_3O_4S$: Calculated: C, 63.43; H, 4.46; N, 9.65; Found: C, 63.18; H, 4.94; N, 9.44.

27. (R)-1,4-Dihydro-2,6-dimethyl-5-nitro-4-[thieno-[3,2-c]pyridin-3-yl]-3-pyridinecarboxylic acid, 1-phenylethyl ester, 26% yield, m.p. 220°-223° C.

Analysis for $C_{23}H_{21}N_3O_4S$: Calculated: C, 63.45; H, 4.83; N, 9.66; Found: C, 63.74; H, 4.92; N, 9.56.

28. 1,4-Dihydro-2,6-dimethyl-5-nitro-4-[thieno[3,2-c]-pyridin-3-yl]-3-pyridinecarboxylic acid, cyclopropylmethyl ester, 6% yield, m.p. 239°-242° C.

Analysis for $C_{19}H_{19}N_3O_4S$: Calculated: C, 59.21; H, 4.97; N, 10.90; Found: C, 59.22; H, 5.16; N, 10.63.

29. 1,4-Dihydro-2,6-dimethyl-5-nitro-4-thieno[3,2-c]-pyridin-3-yl]-3-pyridinecarboxylic acid, 1-cyclopropylethyl ester, 14% yield, m.p. 210°-221° C.

Analysis for $C_{20}H_{21}N_3O_4S$: Calculated: 60.13; H, 5.30; N, 10.52; Found: 60.09; H, 5.24; N, 10.73.

30. 1,4-Dihydro-2,6-dimethyl-5-nitro-4-[thieno[3,2-c]-pyridin-3-yl]-3-pyridinecarboxylic acid, 2-cyanoethyl ester, 25% yield, m.p. 217°-218° C.

Analysis for $C_{18}H_{16}N_4O_4S$: Calculated: C, 56.24; H, 4.20; N, 14.57; Found: C, 56.27; H, 4.28; N, 14.29.

The compounds of the present invention (as isomeric mixtures) act as calcium channel agonists to increase cardiac contractibility and calcium channel antagonists producing a range of activity from no change in, or a decrease in vascular resistance. Individual enantiomers may produce calcium agonist activity such as increasing cardiac contractility and vascular tone or calcium antagonist activity such as decreasing cardiac contractility and vascular tone. These pharmacological activities were examined in the following in vivo model.

Beagle dogs (8.7 to 13.0 kg) were anesthetized with sodium pentobarbital (35 mg/kg) followed by constant infusion of 0.1 mg/kg/minute. Animals were respired through a cuffed endotracheal tube at approximately 20 ml/kg/cycle and 12 cycles/minute. Temperature was maintained at 37°-38° C. using a water-filled heating pad. Polyethylene cannulae were placed in the femoral artery and left ventricle through the common carotid. Pressures were measured using pressure transducers and a strip chart recorder and a computer which gave values for femoral systolic, diastolic, and mean pressure, the rate of increase in left ventricular dP/dt measured at 60 mm Hg, and left ventricular end diastolic pressure. Cardiac output was measured with a thermal dilution catheter and cardiac output computer. From lead II ECG QT intervals were obtained. The QT interval was corrected for heart rate by Bezett's formula, $QT_c = QT/RR^{\frac{1}{2}}$ where the RR interval (sec) = 60/heart rate. Systemic vascular resistance was calculated as mean arterial pressure divided by cardiac output; and double product as systolic arterial pressure times heart rate.

Non-cumulative dose-response curves were obtained for each compound in Table I by administering successive bolus doses of a given compound every 5 minutes. Measurements were made at 2 minutes after each dose. One to six dogs were tested for each compound. Values reported are those concentrations (in micrograms per kilogram) of test compound which: (a) increased left ventricular dP/dt (LVdP/dt) by 30%; (b) decreased vascular resistance (VR) by 30%; and (c) decreased heart rate (HR) by 10% (each value estimated by loglinear interpolation). When such values were not achieved in the dose range tested, they are listed in Table I as being greater than the maximal dose tested.

TABLE I

| Compound Example No. | LVdP/dt | VR | HR |
|---|---|---|---|
| 2 | >1500 | >1500 | 152 |
| 3 | 8814 | 9827 | 1682 |
| 4 | 1606 | 547 | 1438 |
| 5 | 2690 | 1140 | 826 |
| 6 | 638 | 440 | 4871 |
| 7 | 937 | >5000 | 2688 |
| 8 | 2349 | 69 | 1115 |
| 9 | >5000 | 174 | >1500 |
| 10 | 1500 | >1500 | 222 |
| 11 | 983 | >1500 | 949 |
| 12 | >5000 | 123 | >5000 |

TABLE I-continued

| Compound Example No. | LVdP/dt | VR | HR |
|---|---|---|---|
| 15 | 643 | >1500 | 258 |
| 18 | >1500 | 97 | 1055 |
| 20 | 1089 | >1500 | 232 |
| 21 | 1126 | >1500 | 436 |
| 22 | >1500 | 1500 | 1263 |
| 23 | >1500 | >1500 | 737 |
| 24 | >1500 | 497 | >1500 |
| 25 | 1995 | >5000 | 1316 |
| 26 | 126 | 94 | 1068 |
| 27 | 155 | 2612 | 805 |
| 28 | 978 | 245 | 2252 |
| 29 | >5000 | 176 | 735 |
| 30 | >1500 | >1500 | >1500 |

A second series of studies assessed the cardiovascular effects of infusion of the compound of Example 27 as compared to its individual diastereomers of Examples 16 (R,R-isomer) and 17 (S,R-isomer). Four treatment groups of dogs (4–6 dogs per each group) were given a 45 minute infusion (0.2 mg/kg/min) of one of the compounds shown in Table II or vehicle (polyethylene glycol-300) at 0.194 ml/minute. The parameters shown were measured at the end of infusion except for baseline values which were measured immediately prior to infusion.

TABLE II

| | CARDIOVASCULAR EVALUATION | | | |
|---|---|---|---|---|
| | LVdP/dt[a] | VR[b] | HR[c] | $QT_c$ |
| Compound Example 27 | | | | |
| Baseline Value | 3221 ± 271 | 6908 ± 462 | 154 ± 7 | 354 ± 7 |
| % Change | 43 ± 15 | −7 ± 4 | −22 ± 3 | 5.4 ± 2.0 |
| Compound Example 16 | | | | |
| Baseline Value | 3027 ± 422 | 7332 ± 567 | 165 ± 3 | 339 ± 11 |
| % Change | 20 ± 9 | 41 ± 16 | −18 ± 2 | 11.6 ± 2.8 |
| Compound Example 17 | | | | |
| Baseline Value | 3125 ± 268 | 8114 ± 728 | 148 ± 12 | 339 ± 12 |
| % Change | 25 ± 15 | −59 ± 6 | −12 ± 12 | −3 ± 1.5 |
| Vehicle Alone | | | | |
| Baseline Value | 3520 ± 244 | 7771 ± 490 | 160 ± 8 | 321 ± 7 |
| % Change | 1 ± 4 | 2 ± 3 | −5 ± 2 | −0.4 ± 0.6 |

[a]Rate of increase in left ventricular pressure at 60 mm Hg expressed in millimeters Hg per second
[b]Vascular resistance expressed in dyne · sec · cm$^{-5}$
[c]Heart rate expressed in beats per minute The compounds of this invention may be administered by any number of routes, including the oral, sublingual, subcutaneous, intramuscular, intravenous, transdermal, and rectal routes. The compounds are usually employed in the form of pharmaceutical compositions. Such compositions are prepared in a manner well known in the pharmaceutical art and comprise from about 1 to about 95 percent by weight of at least one active compound of the above Formula I.

Such pharmaceutical compositions comprise as active ingredient a compound of the above formula associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing an effective amount of one or more compounds of formula I, typically from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The compounds of the present invention are effective over a wide dosage range. For example, effective amounts of said compounds will normally fall within the range of about 0.005 to about 50 mg/kg of body weight per day. In the treatment of adult humans, the range of about 0.001 to about 20 mg/kg, in single or divided doses per day, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and, therefore, the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above Formula (I) and pharmaceutically acceptable salts thereof.

EXAMPLE 31

Hard gelatin capsules are prepared using the following ingredients:

|  | per capsule |
|---|---|
| (R,d)-1,4-dihydro-2,6-dimethyl-5-nitro-4-[thieno[3,2-c]pyridin-5-yl]-3-pyridinecarboxylic acid, l-phenylethyl ester | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 32

Tablets each containing 10 mg of active ingredient are made up as follows:

|  | per tablet |
|---|---|
| (R,l)-1,4-dihydro-2,6-dimethyl-5-nitro-4-[thieno[3,2-c]pyridin-3-yl]-3-pyridinecarboxylic acid, l-phenylethyl ester | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. Sieve, are then added to the granules.

EXAMPLE 33

Suppositories each containing 25 mg of active ingredient are made as follows:

|  | per suppository |
|---|---|
| (S)—1,4-dihydro-2,6-dimethyl-5-nitro-4-[thieno[3,2-c]pyridin-3-yl]-3-pyridinecarboxylic acid, l-phenylethyl ester | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 34

Suspensions each containing 5 mg of medicament per 5 ml dose are made as follows:

|  | per 5 ml of suspension |
|---|---|
| 1,4-dihydro-2,6-dimethyl-5-nitro-4-[thieno[3,2-c]pyridin-3-yl]-3-pyridinecarboxylic acid, | 5 mg |

-continued

|  | per 5 ml of suspension |
|---|---|
| 2-propynyl ester |  |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

Further information pertaining to pharmaceutical formulations may be obtained Remington's Pharmaceutical Sciences, 17th Edition 1985, which is incorporated herein by reference.

We claim:

1. A compound of the formula

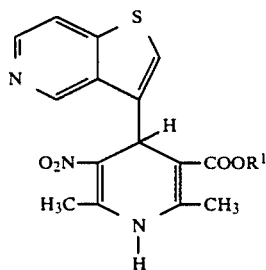

and pharmaceutically acceptable salts thereof wherein $R^1$ is a straight or branched chain, saturated or unsaturated aliphatic radical containing from one to six carbon atoms, both inclusive, optionally substituted with one or more groups selected from phenyl, methoxy-substituted phenyl, phenoxy, methoxy or cyclopropyl; or $R^1$ is cyanoethyl.

2. The compound of claim 1 which is 1,4-dihydro-2,6-dimethyl-5-nitro-4-[thieno[3,2-c]pyridin-3-pyridinecarboxylic acid, 1-phenylethyl ester.

3. The compound of claim 1 which is 1,4-dihydro-2,6-dimethyl-5-nitro-4-thieno[3,2-c]pyridin-3-pyridinecarboxylic acid, 1-methyl-2-propynyl ester.

4. The compound of claim 1 which is 1,4-dihydro-2,6-dimethyl-5-nitro-4-[thieno[3,2-c]pyridin3-yl]-3-pyridinecarboxylic acid, cyclopropylmethyl ester.

5. A method of treating congestive heart failure in a mammal in need thereof comprising administering to said mammal an effective amount of a compound of the formula

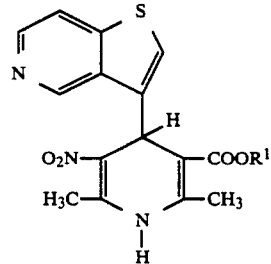

and pharmaceutically acceptable salts thereof wherein $R^1$ is a straight or branched chain, saturated or unsaturated aliphatic radical containing from one to six carbon atoms, both inclusive, optionally substituted with one or more groups selected from phenyl, methoxy-substituted phenyl, phenoxy, methoxy or cyclopropyl; or $R^1$ is cyanoethyl.

6. The method of claim 5 wherein the compound employed is 1,4-dihydro-2,6-dimethyl-5-nitro-4-[thieno[3,2-c]pyridin-3-yl]-3-pyridinecarboxylic acid, 1-phenylethyl ester.

7. The method of claim 5 wherein the compound employed is 1,4-dihydro-2,6-dimethyl-5-nitro-4-[thieno[3,2-c]pyridin-3-yl]-3-pyridinecarboxylic acid, 1-methyl-2-propynyl ester.

8. The method of claim 5 wherein the compound employed is 1,4-dihydro-2,6-dimethyl-5-nitro-4-[thieno3,2-c]pyridin-3-yl]-3-pyridinecarboxylic acid, cyclopropylmethyl ester.

9. A pharmaceutical formulation for use in treating congestive heart failure comprising an effective amount of a compound of the formula

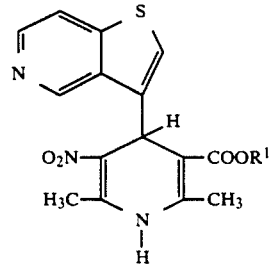

and pharmaceutically acceptable salts thereof wherein $R^1$ is a straight or branched chain, saturated or unsaturated aliphatic radical containing from one to six carbon atoms, both inclusive, optionally substituted with one or more groups selected from phenyl, methoxy-substituted phenyl, phenoxy, methoxy or cyclopropyl; or $R^1$ is cyanoethyl in admixture with one or more pharmaceutically acceptable carriers, diluents or excipients therefor.

10. The formulation of claim 9 wherein the compound employed is 1,4-dihydro-2,6-dimethyl-5-nitro-4-[thieno[3,2-c]pyridin-3-yl]-3-pyridinecarboxylic acid, 1-phenylethyl ester.

11. The formulation of claim 9 wherein the compound employed is 1,4-dihydro-2,6-dimethyl-5-nitro-4-[thieno[3,2-c]pyridin-3-yl]-3-pyridinecarboxylic acid, 1-methyl-2-propynyl ester.

12. The formulation of claim 9 wherein the compound employed is 1,4-dihydro-2,6-dimethyl-5-nitro-4-[thieno[3,2-c]pyridin-3-yl]-3-pyridinecarboxylic acid, cyclopropylmethyl ester.

* * * * *

UNITED STATES PATENT AND TRADEMARK OFFICE
CERTIFICATE OF CORRECTION

PATENT NO. : 4,902,694
DATED : February 20, 1990
INVENTOR(S) : Donald R. Holland and James H. Wikel It is certified that error appears in the above-identified patent and that said Letters Patent is hereby corrected as shown below:

Column 11, line 54, "pyridin-3-pyridinecar-" should read --pyridin-3-yl]-3-pyridinecar- --.

Column 11, line 57, "pyridin-3-pyridinecar-" should read --pyridin-3-yl]-3-pyridinecar- --.

Signed and Sealed this

Second Day of July, 1991

*Attest:*

HARRY F. MANBECK, JR.

*Attesting Officer*   *Commissioner of Patents and Trademarks*